(12) United States Patent
Hyde et al.

(10) Patent No.: US 8,029,727 B2
(45) Date of Patent: Oct. 4, 2011

(54) EVENT-TRIGGERED SELF-STERILIZATION OF ARTICLE SURFACES

(75) Inventors: Roderick A. Hyde, Redmond, WA (US); Muriel Y. Ishikawa, Livermore, CA (US); Jordin T. Kare, Seattle, WA (US); Elizabeth A. Sweeney, Seattle, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 555 days.

(21) Appl. No.: 12/286,450

(22) Filed: Sep. 29, 2008

(65) Prior Publication Data
US 2010/0008819 A1    Jan. 14, 2010

Related U.S. Application Data

(63) Continuation-in-part of application No. 12/218,214, filed on Jul. 11, 2008.

(51) Int. Cl.
| | |
|---|---|
| B01J 19/00 | (2006.01) |
| A61L 2/00 | (2006.01) |
| B08B 7/00 | (2006.01) |
| B08B 9/20 | (2006.01) |
| B08B 9/00 | (2006.01) |
| A47L 15/00 | (2006.01) |
| A47L 1/02 | (2006.01) |

(52) U.S. Cl. .............. 422/28; 422/1; 422/40; 422/292; 422/300; 422/301; 134/6; 134/25.1; 134/42; 15/97.1; 15/1; 15/3.5; 15/77

(58) Field of Classification Search .............. 422/1, 28, 422/40, 292, 300–301; 134/6, 25.1, 42; 15/97.1, 15/1, 3.5, 77
See application file for complete search history.

(56) References Cited

U.S. PATENT DOCUMENTS

| | | | |
|---|---|---|---|
| 2,602,724 | A | 7/1952 | Batchelor |
| 4,296,068 | A | 10/1981 | Hoshino |
| 5,164,164 | A | 11/1992 | Strickler et al. |
| 5,367,720 | A | 11/1994 | Stephens et al. |
| 5,630,379 | A | 5/1997 | Gerk et al. |
| 5,771,528 | A | 6/1998 | Nappi, Sr. |
| 5,820,821 | A | 10/1998 | Kawagoe et al. |
| 7,570,018 | B2 | 8/2009 | Waguespack |
| 2007/0074672 | A1 | 4/2007 | Torgerson et al. |
| 2007/0207073 | A1 | 9/2007 | Drucker |
| 2008/0056933 | A1 | 3/2008 | Moore et al. |

OTHER PUBLICATIONS

PCT International Search Report; International App. No. PCT/US 09/04028; Sep. 10, 2009; pp. 1-2.
Albert, Richard K. and Condie, Frances; "Medical Intelligence: Hand-Washing Patterns in Medical Intensive-Care Units"; New England Journal of Medicine; Jun. 1981; pp. 1465-1466; vol. 304, No. 24.

*Primary Examiner* — Jill Warden
*Assistant Examiner* — Monzer Chorbaji

(57) ABSTRACT

Solutions for limiting the undesirable spread of pathogens by indirect contact are provided. The solutions involve event-controlled self-sterilization of contact surfaces on articles or fixtures. A self-sterilizing contact surface structure allows chemical sterilizing agents to controllably flow in response to a contact event, from within the article to exude upon a portion of the contact surface.

45 Claims, 6 Drawing Sheets

EVENT-TRIGGERED SELF-STERILIZATION OF ARTICLE SURFACES

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 12/218,214, entitled EVENT-TRIGGERED SELF-STERILIZATION OF ARTICLE SURFACES, naming Roderick A. Hyde; Muriel Y. Ishikawa; Jordin T. Kare; Elizabeth A. Sweeney and Lowell L. Wood, Jr. as inventors, filed 11, Jul., 2008, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

BACKGROUND

Diseases and infections can be transmitted by indirect contact. Any contact surface, which is touched by more than one person, can be a transfer point for harmful germs spreading diseases and infections through a population. An example is the common cold. A person, who has a cold, can leave cold virus behind on a door handle he or she touches. A non-infected person, who later touches the door handle, can pick up the cold virus from the door handle and catch the same cold.

For certain high risk environments (e.g., restrooms, food service and health care facilities), public health programs recommend hand washing or hand rubbing routines for maintaining good hand hygiene to prevent or reduce propagation of communicable diseases and infections. However, time and facilities constraints present are major obstacles to maintaining good hand hygiene. Many studies of nosocomial infections show that hand washing protocols are not properly followed even by health care providers. General compliance rates of health care providers with hospital-recommended hand washing or hand rubbing protocols are low. The poor compliance rates have been attributed in part to a lack of knowledge of when and how to clean or disinfect hands, and in part to time constraints and poor access to hand washing facilities or hand rubbing products. (See e.g., Albert R. K., Condie F., NEJM 1981; 304(24):1465-6).

The time and facilities constraints that impede good hand hygiene in hospital environments are even more severe obstacles for achieving good hand hygiene in other public environments. For example, it is not practical to provide hand washing facilities at every door knob or entrance in a working office building, or at every turnstile or contact surface in a bus or train terminal. Further, even where hand washing facilities are provided (e.g., in restrooms), hand washing can be counterproductive. A person, after washing hands, could pick up germs by turning a water faucet handle off, or touching a restroom exit door handle.

Consideration is now being given to other solutions for limiting the undesirable spread of pathogens by indirect contact. Some such solutions may avoid, for example, the time and facilities constraints that hinder solutions that rely on voluntary hand washing by individuals.

SUMMARY

Approaches to limiting the spread of pathogens, for example, by indirect contact are provided. One approach utilizes self-sterilizing contact surface structures. A self-sterilizing contact surface structure may be disposed on any article, fixture or substrate in any environment, which can be touched by a person.

In one approach, the self-sterilizing contact surface structure includes an exterior contact surface, which can be touched, and an interior chemical flow-conductive region which is contiguous to the exterior contact surface. The self-sterilizing contact surface structure is configured so that a sterilizing chemical agent can be controllably transconducted across the interior chemical flow-conductive region on to at least a portion of the exterior contact surface. The self-sterilizing contact surface structure includes egress ports or openings through which transconducted sterilizing chemical agent can exude on to the exterior contact surface. The flow of the sterilizing chemical agent to the exterior contact surface can be triggered by specific events (e.g., contact, imminent contact, or lapse of time).

The self-sterilizing contact surface structure may include one or more sensors (e.g., contact sensor, a proximity sensor, or a chemical sensor) which are configured to detect if a contact has occurred or is likely, or if biomaterials are present on the exterior contact surface. Further, the structure may include, or be coupled to, control elements that control, time or regulate the flow of the sterilizing chemical agent on to the contact surface in response to events. The control elements may act in response to, for example, sensor information, contact surface activity, and/or other control signals. Additionally, the structure may include, or be coupled to, a power source/receiver, which provides energy for the controlled flow of the sterilizing chemical agent. Like the control elements, the power source/receiver may be responsive to sensor information, contact surface activity, and/or control signals. A contact surface status indicator coupled to the structure may display a sterilization condition or state of the contact surface to users. Similarly, a refill indicator coupled to the structure may display a refill state of the sterilizing chemical supply.

The foregoing summary is illustrative only and is not intended to be limiting. In addition to the illustrative aspects, embodiments, and features described above, further aspects, embodiments, and features of the solutions will become apparent by reference to the drawings and the following detailed description.

BRIEF DESCRIPTION OF THE FIGURES

In the accompanying drawings.

Throughout the figures, unless otherwise stated, the same reference numerals and characters are used to denote like features, elements, components, or portions of the illustrated embodiments.

DESCRIPTION

In the following description of exemplary embodiments, reference is made to the accompanying drawings, which form a part hereof. It will be understood that embodiments described herein are exemplary, but are not meant to be limiting. Further, it will be appreciated that the solutions described herein can be practiced or implemented by other than the described embodiments. Modified embodiments or alternate embodiments may be utilized, in the sprit and scope of the solutions described herein.

Figure 1:
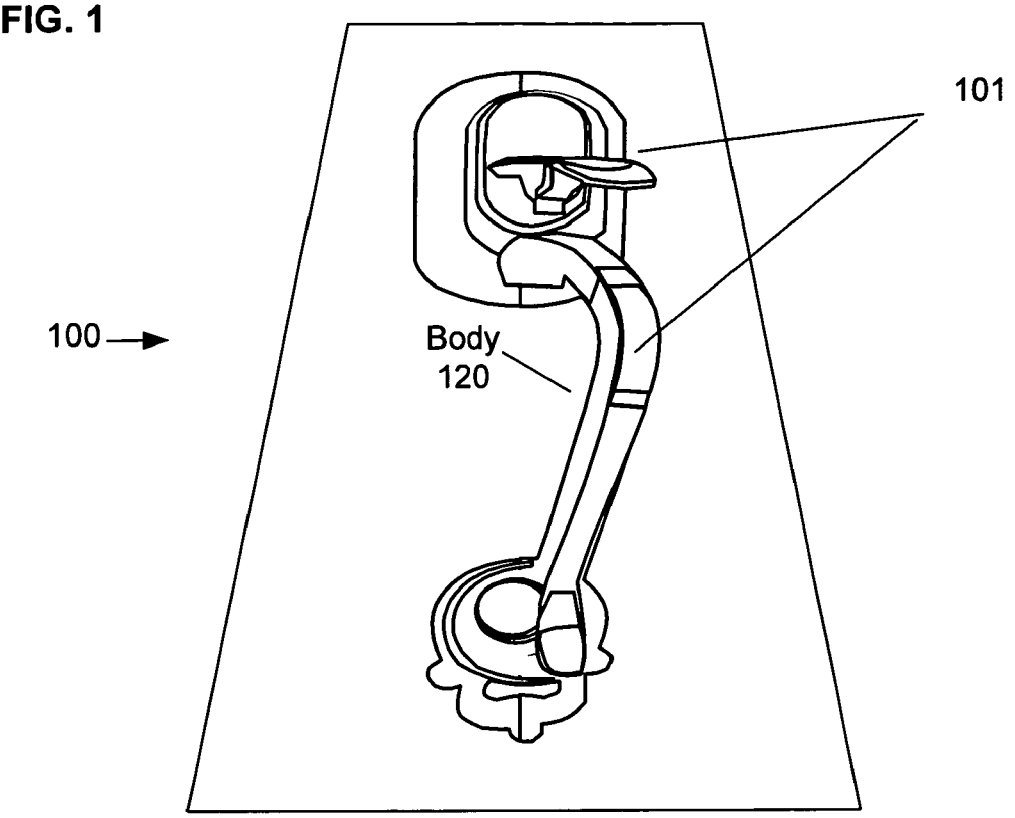
FIG. 1 is a schematic illustration of exemplary self-sterilizing articles or fixtures, which have contact surfaces that are self-sterilized to prevent or reduce the spread of communicable diseases and infections by indirect contact, in accordance with the principles of the solutions described herein.
Figure 1:
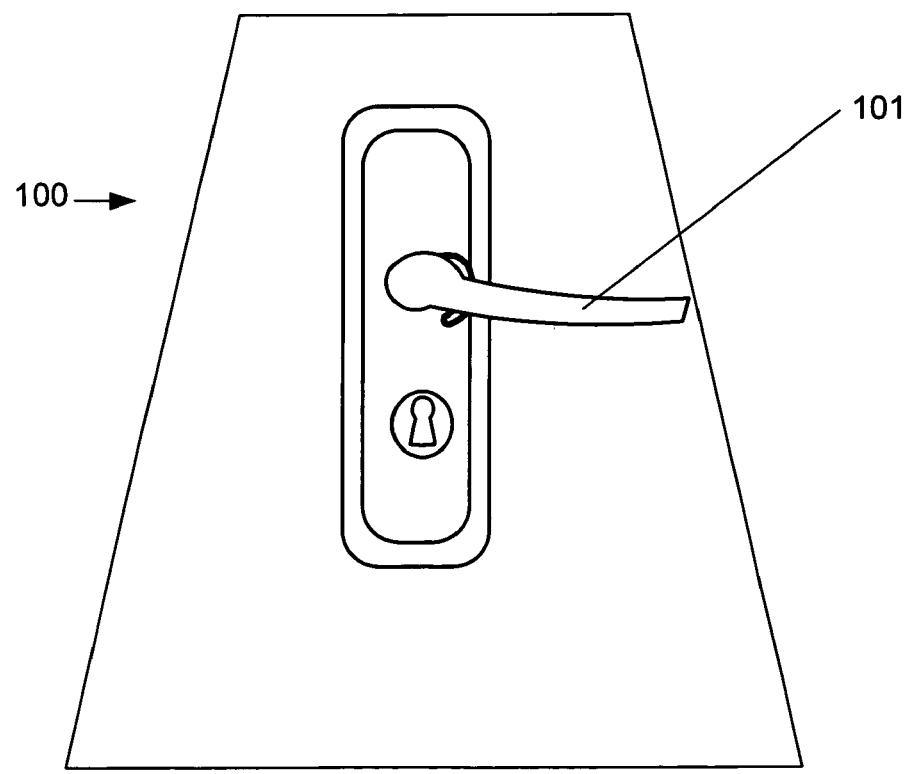

FIGS. 1-4 show exemplary self-sterilizing articles 100, each having an article body 120 with a contact surface 101 disposed thereon. Exemplary articles 100, as shown for purposes of illustration in FIG. 1, are door handles having particular shapes. Article 100 may, however, be any device or fixture of any shape having one or more surfaces that can be touched or contacted in use. Article 100 may, for example, be a handle, a hand rail, a seat, a key board, a switch, a button, a knob, a computer mouse or control device, a desktop, a bathroom or kitchen or other working surface, a bus seat, a gymnasium apparatus or fixture, a restaurant booth or seat, a toy, a headphone, a telephone, an automatic teller machine, a vending machine, a shopping cart, a household device or fixture, a building device or fixture, an industrial device or fixture, a transport vehicle device or fixture, a medical device or fixture, or any other device or fixture whose contact surfaces are sites for potential transfer of undesirable pathogens amongst users.

Figure 2:
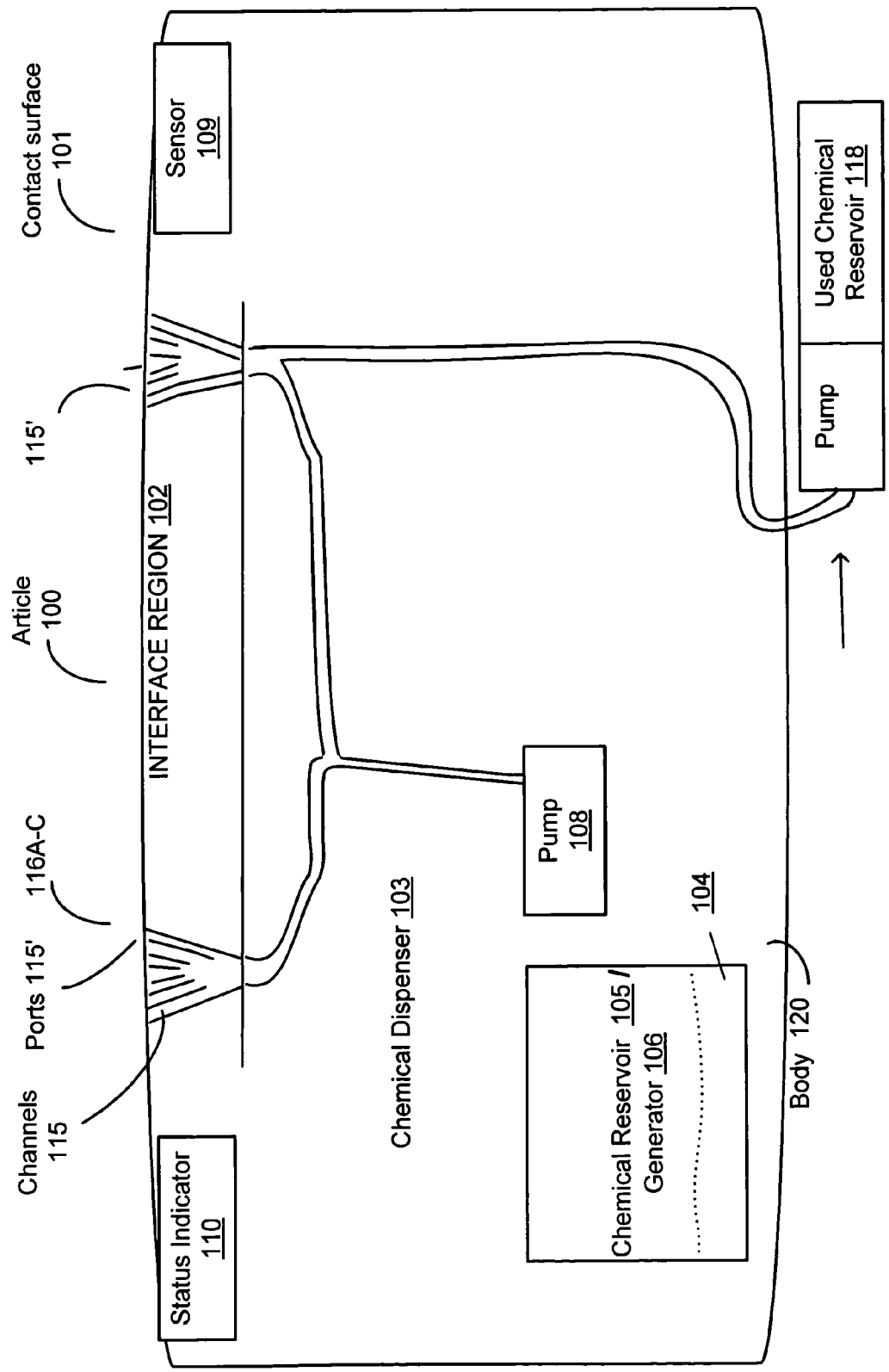
FIG. 2 is a block diagram illustrating an exemplary system for dispensing sterilizing agent in an article or fixture having a self-sterilizing contact surface, in accordance with the principles of the solutions described herein.

With reference to FIG. 2, self-sterilizing article 100 is coupled to a chemical dispenser system 103, which is arranged to controllably dispense or deliver a chemical 104 on to contact surface 101 from within body 120. Chemical 104 may, for example, be a sterilizing chemical, which reduces or kills pathogens (e.g., bacteria, viruses, or germs), which may be present on contact surface 101. Suitable sterilizing chemicals 104 may, for example, include one or more of inorganic or organic compounds, oxidizers, halogens, alcohols, amine- or hypochlorite-based chemicals, or any other germicidal chemicals or compounds. Chemical 104 may be dispensed in any suitable physical state (e.g., solid, gas, liquid or gel). Preferably, sterilizing chemical 104 is such that it vaporizes or sublimes from contact surface 101 after delivery without leaving behind any substantial residues.

Pre-prepared chemical 104, which is ready for dispensing, may be obtained from a chemical reservoir 105. Alternatively, chemical 104 may be prepared in situ, for example, in a chemical generator 106. For example, chemical 104 may be chlorine gas, or liquid bleach prepared by self-liquefaction of a mixture of calcium hypochlorite ($Ca(OCl)_2$) laced with calcium chloride ($CaCl_2$) in chemical generator 106 (e.g., under contact-induced pressure).

In operation, controlled amounts of chemical 104 are dispensed or delivered by chemical dispenser system 103 onto contact surface 101 from within article 100. For this purpose, chemical dispenser system 103 may include, or be linked to a source of chemical 104 (e.g., reservoir 105/generator 106). The chemical source may be internal to article 100/body 120, as shown, for example, in FIG. 2. Alternatively, the chemical source of chemical 104 may be external to article 100/body 120, as shown for example, in FIG. 4. Thus, in the example of a building door handle article, the chemical source may be placed in the door handle itself, the door, or any other part of the building structure.

In any case, suitable conductive passageways or channels 115 that cross interface region 102 guide a flow of chemical 104 obtained from the chemical source onto contact surface 101, which has suitable surface ports or openings 115' for egress of chemical 104. Surface ports or openings 115' may be distributed over the entire area of contact surface 101. Alternatively, contact surface 101 may be patterned so that surface ports or openings 115' are present only in select regions (e.g., regions 116A-C) while other regions (e.g., region 117) are free of such ports or openings (see FIG. 3).

Embodiments of chemical dispenser system 103 may include, or operationally interface with, one or more other electrical and/or mechanical components configured to recognize and respond to events, and control the flow of chemical 104. For example, chemical dispenser system 103 may optionally include a controller 107, a pumping mechanism 108, a sensor 109, a status/refill indicator 110, a timer 111, a counter 112, a power source/receiver 113, and/or a programmable interface 114. Like chemical reservoir 105 described above, each of these optional components may be disposed either inside or outside article 100 (see FIG. 4).

Figure 4:
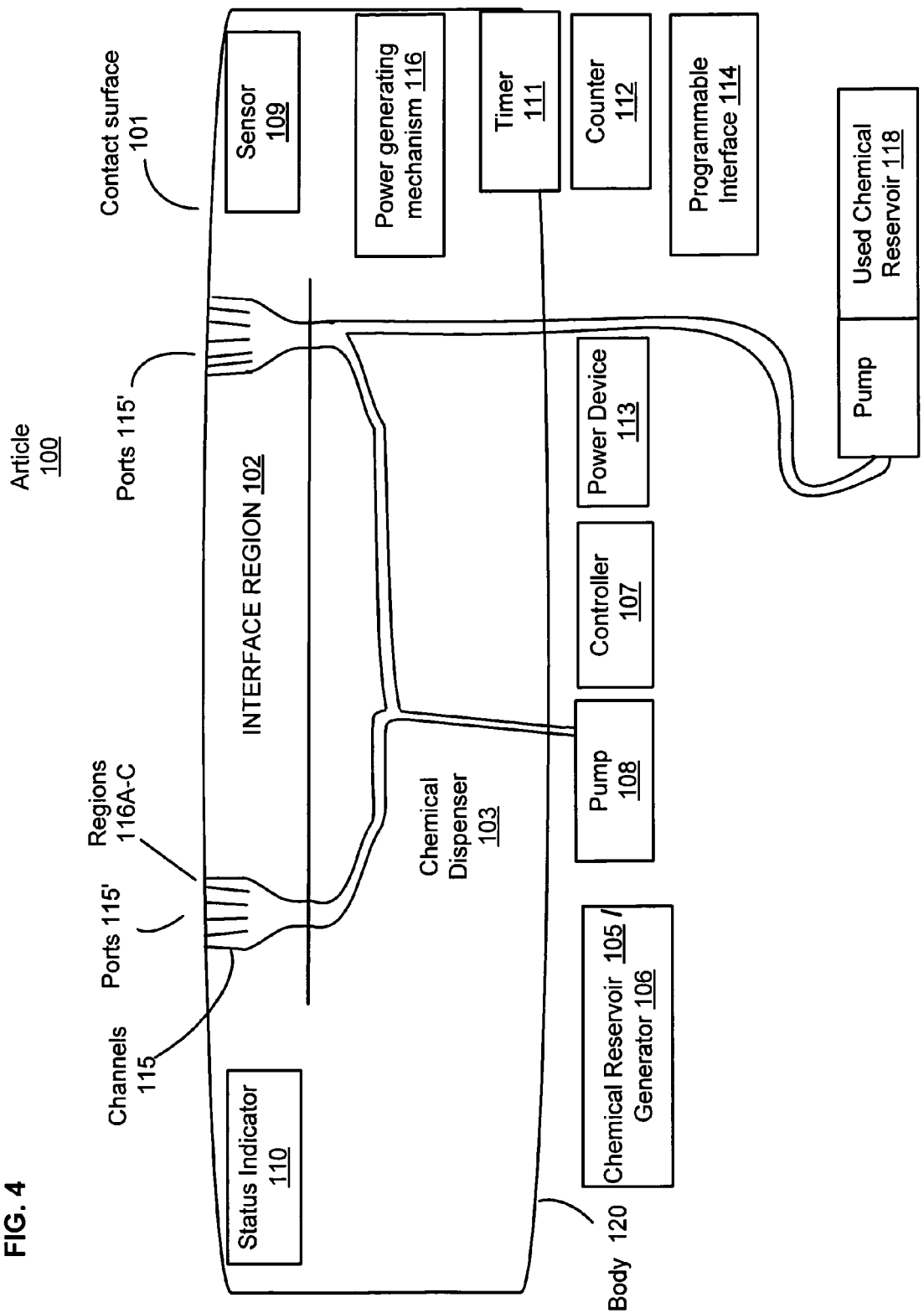
FIG. 4 is a block diagram illustrating an arrangement of exemplary control elements that control or regulate flow of a sterilizing chemical to the self-sterilizing contact surface of FIGS. 1-3, in accordance with the principles of the solutions described herein.

With reference to FIGS. 2 and 4, the flow of chemical 104 across the interface 102 onto contact surface 101 is driven by pumping or regulating mechanism 108. Pumping mechanism 108 may, for example, be an electromechanical pump. Alternative versions of pumping mechanism 108 may, for example, include elasticity- or strain-, mechanical-, pressure-, temperature-, surface tension-, osmotic pressure-, and/or gravity-actuated prime movers.

Suitable energy or power for operating pumping mechanism 108 may be obtained from an internal or external power source/receiver 113 (e.g., a dry cell or a wound spring or resonant inductive power reception circuitry). Further, operation or movement of article 100 itself may be utilized to generate energy or power for driving pumping mechanism 108 or other components of chemical dispenser system 103. For example, contact-induced pressure and/or contact-induced temperature may be utilized to drive or regulate the flow of chemical 104 (e.g., using a pressure- or temperature-activated flow switch).

Additionally or alternatively, article 100 may be coupled to an energy- or power-generating mechanism (e.g., generator 116). Generator 116 may, for example, couple mechanical movement of article 100 (e.g., turning of a door handle, or opening of a door) to drive pumping mechanism 108 directly. For this purpose, generator 116 may include any suitable mechanical coupling arrangement (e.g., levers and springs). Alternatively, generator 116 may be configured to convert mechanical movement of article 100 into storable elastic, electrical or other energy. Generator 116 may include any suitable mechanical and/or electromechanical converter arrangements (e.g., springs, coils, inductors, and magnets) for this purpose. The energy generated in this manner by generator 116 may be used either directly to drive pumping mechanism 108, or stored for later use (e.g., in power source/receiver 113).

Chemical dispensing system 103 including pumping mechanism 108 may include flow-regulating features (e.g., pressure-activated flow switches, and orifices and channels having predetermined flow-impedance) to control timing and delivery amounts of chemical 104 to contact surface 101. More generally, the operation of chemical dispensing system 103 may be supervised by a control device or system.

Chemical dispensing system 103 also may include, or be coupled to, a used chemical recovery or disposal system that is arranged to collect residual chemicals from contact surface 101. An exemplary used chemical recovery/disposal system may include a used-chemical reservoir 118, which is gravity-fed. Another exemplary used chemical recovery/disposal system may include a heater arrangement (not shown) to vaporize residual chemicals from contact surface 101.

FIG. 4 shows an exemplary controller 107 configured to supervise operation of chemical dispensing system 103. Controller 107 may have any suitable mechanical or electromechanical structure, and include an optional programmable interface 114. In operation, controller 107 may control timing and amounts of chemical 104 delivered to contact surface 101 in response to one or more event-triggered control signals. The event-triggered control signals may be generated by one or more control elements. The control elements may, for example, include one or more of sensor 109, timer 111, counter 112, or a user-activated switch (not shown). As noted previously, each of these control elements may be disposed either inside or outside article 100.

Sensor 109 may be a contact sensor which is configured to determine if a contact has been made to contact surface 101 and to accordingly generate a control signal to activate chemical dispenser system 103 directly, or via controller 107, to provide chemical 104 across interface region 102. The contact sensor may, for example, be any of a capacitive, a resistive, a thermal, a mechanical, a piezoelectric, an ultrasonic, an electromagnetic, or an optical sensor.

Additionally or alternatively, sensor 109 may be a proximity sensor arranged to determine if a contact to contact surface 101 is likely, and to accordingly generate a control signal to activate chemical dispenser system 103 directly, or via controller 107, to provide chemical 104 across interface region 102. Like the contact sensor, the proximity sensor may, for example, be any of a capacitive, a resistive, a thermal, a mechanical, a piezoelectric, an ultrasonic, an electromagnetic, or an optical sensor.

Further, sensor 109 may be a bio- or chemical sensor arranged to determine a presence of biological materials (e.g., sweat, lipids, etc.) on contact surface 101, and to accordingly generate a control signal to activate chemical dispenser system 103 directly, or via controller 107, to provide chemical 104 across interface region 102.

Figure 3:
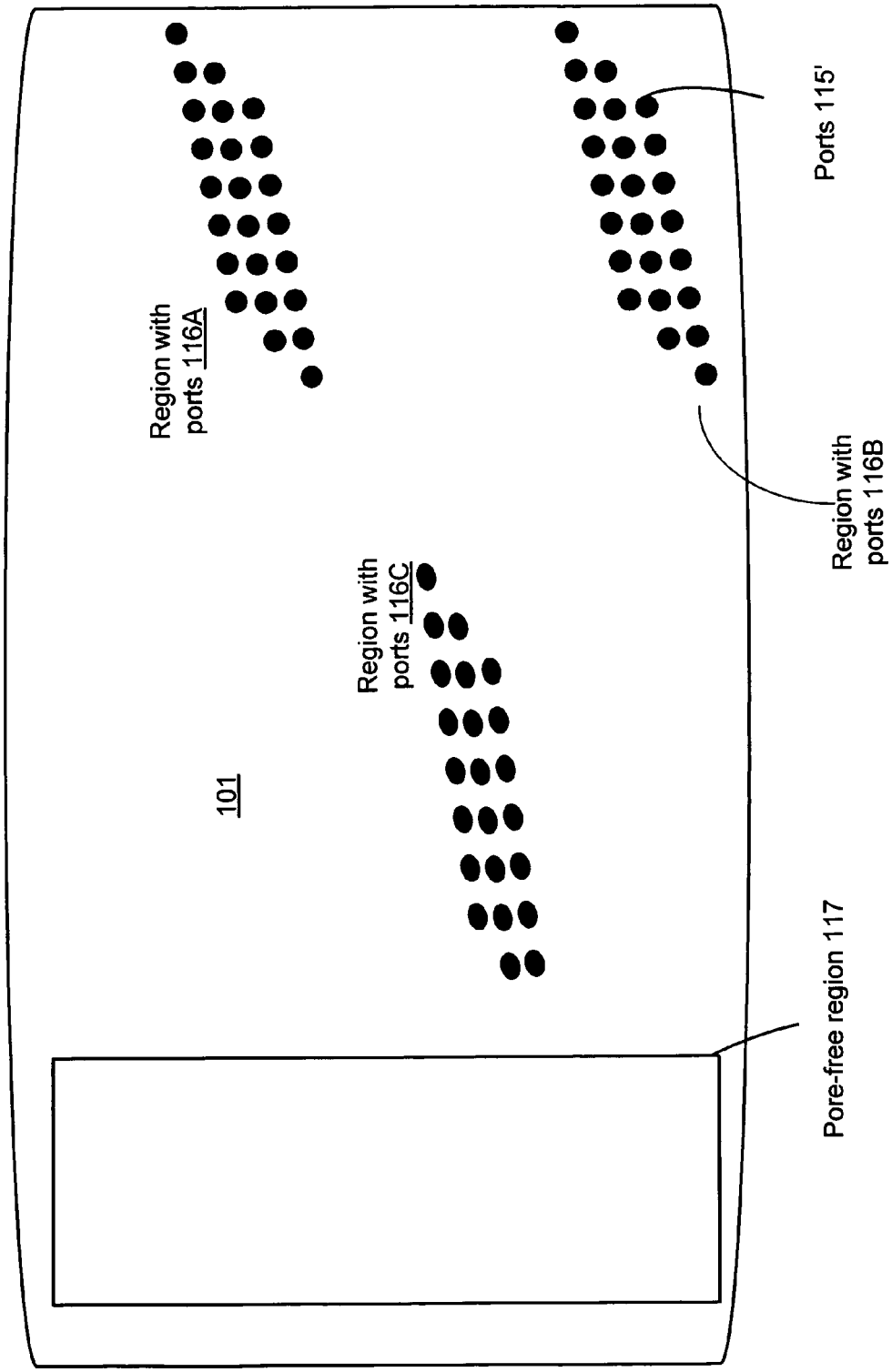
FIG. 3 is a schematic illustration of the self-sterilizing contact surface of FIG. 1, in accordance with the principles of the solutions described herein.

FIGS. 2 and 4, for visual clarity, show a solitary sensor 109. However, it will be understood that any suitable numbers of sensors of various types may be deployed. Further, the sensor(s) may be configured to identify particular portions or sub regions of contact surface 101 of interest, and to accordingly activate dispenser system 103 directly, or via controller 107, to provide chemical 104 across interface region 102 only to those particular portions or subregions if so desired. For example, sensor 109, in addition to determining if a contact is made, may be further configured to determine a location of contact. With reference to FIG. 3, such a sensor 109 may, for example, determine that only subregion 116B of contact surface 101 has been contacted or touched. Accordingly, chemical dispenser system 103 may be activated to provide chemical 104 only to subregion 116B, if so desired. Alternatively, chemical dispenser system 103 may be activated to provide chemical 104 to all subregions 116A-C of contact surface 101 even though only subregion 116B has been contacted or touched.

Control elements such as timer 111 or counter 112 also may generate alternate or additional event-triggered control signals to activate chemical dispenser system 103 only at certain times and/or only for particular durations. For example, counter 112, which may be an indexed or resettable counter, may count a number of contacts made, and activate chemical dispenser system 103 to provide chemical 104 each time the counted number equals or exceeds a predetermined number. Similarly, controller 107 may be coupled to timer 111, which clocks or times the provision of chemical 104 across interface 102. Controller 107 may be further configured to respond to various sensor signals so that provision of chemical 104 across interface 102 begins a predetermined time interval after a contact is made, before a contact is made, or during a contact. In any case, the provision of chemical 104 may be continuous for a predetermined time interval after a triggering event.

Alternatively or additionally, controller 107 may be further configured to control provision of chemical 104 across interface 102 according to predetermined schedules. A predetermined schedule may be independent of the state or condition of contact surface 101. For example, a predetermined schedule may ask for chemical 104 to be released every ten minutes, independent of the number of contacts made in the interim. Alternative predetermined schedules may be flexible or adjustable to take into consideration events, including without limitation, events potentially affecting contact surface 101. For example, chemical 104 may be scheduled to be routinely released every ten minutes, but the schedule may be advanced or supplemented if a number of contacts made in the interim exceeds three. Similarly, timing or amount of release of chemical 104 may be responsive to a number of persons in a region proximate the contact surface 101 or to other environmental events (e.g. changes in heating, ventilation, and air conditioning (HVAC) operation in the area or building). Moreover, the schedule, amount, or other aspects of release of chemical 104 may be controlled by controller 107 or other controller systems that may be located nearby or distant from contact surface 101. In one approach, for example, the schedule, amount, or other aspects of release of the sterilizing chemical 104 may be controlled through a remote control system in a different building or facility, for example, through wireless, wired, IP protocol or other approaches.

The predetermined schedules and the responses of chemical dispensing system 103/controller 107 to various control signals may be set up or programmed by a user, for example, through programmable interface 114.

Article 100 also may include an optional status indicator 110, which is configured to indicate a state of the contact surface and/or chemical dispensing system 103. Status indicator 110 may, for example, include a set of red, yellow and green color light emitting diodes corresponding to various sterilization states of contact surface as determined by one or more sensors or control elements. Other versions of status indicator 110 may include other visual, audio, RF or electromagnetic and/or tactile displays of the contact surface state. Similarly, the same or another status/refill indicator 110 may display a state of chemical dispensing system 103 (e.g., refill state of a chemical reservoir).

Figure 5:
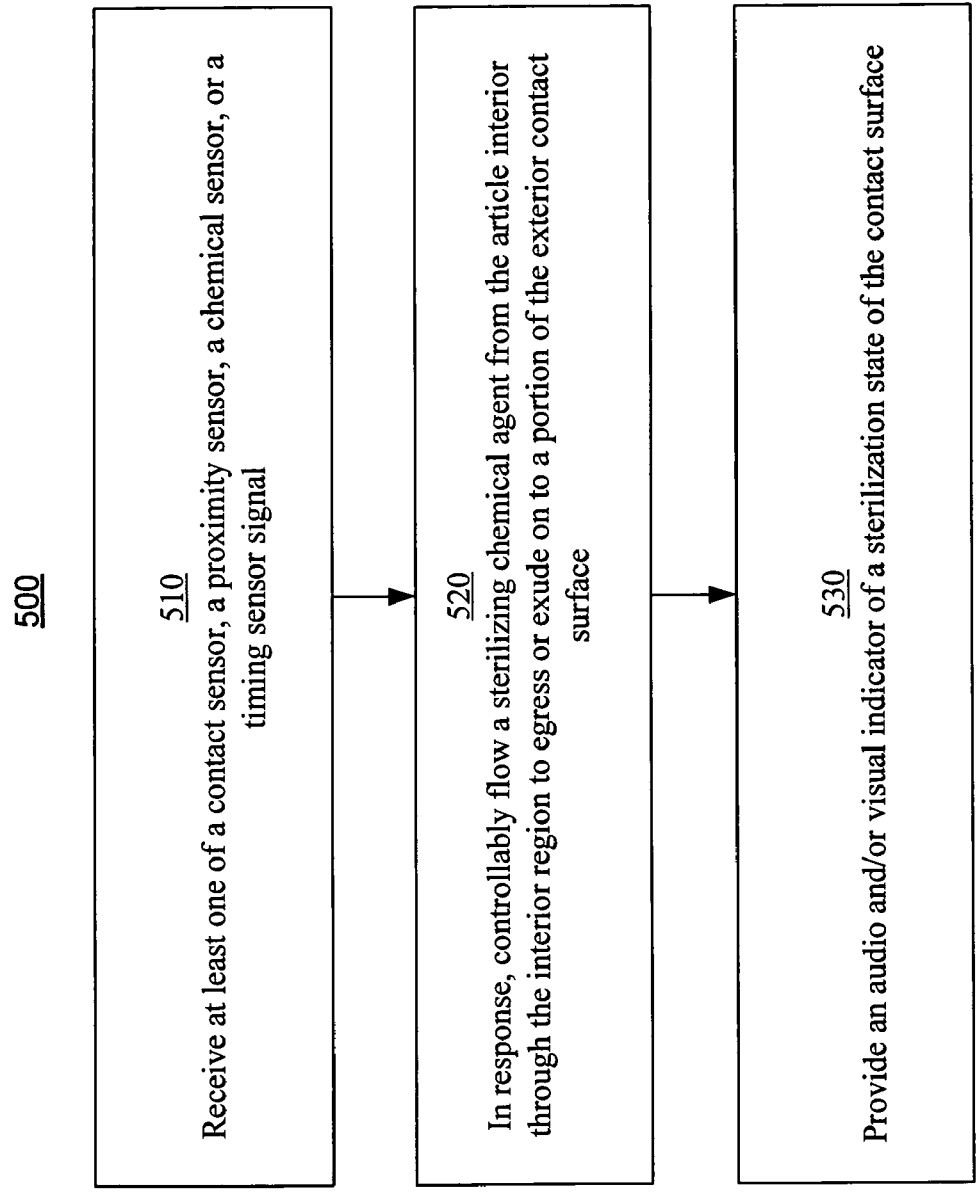
FIGS. 5 and 6 are flow diagrams illustrating exemplary methods for inhibiting the spread of germs by indirect contact, in accordance with the principles of the solutions described herein.
Figure 6:
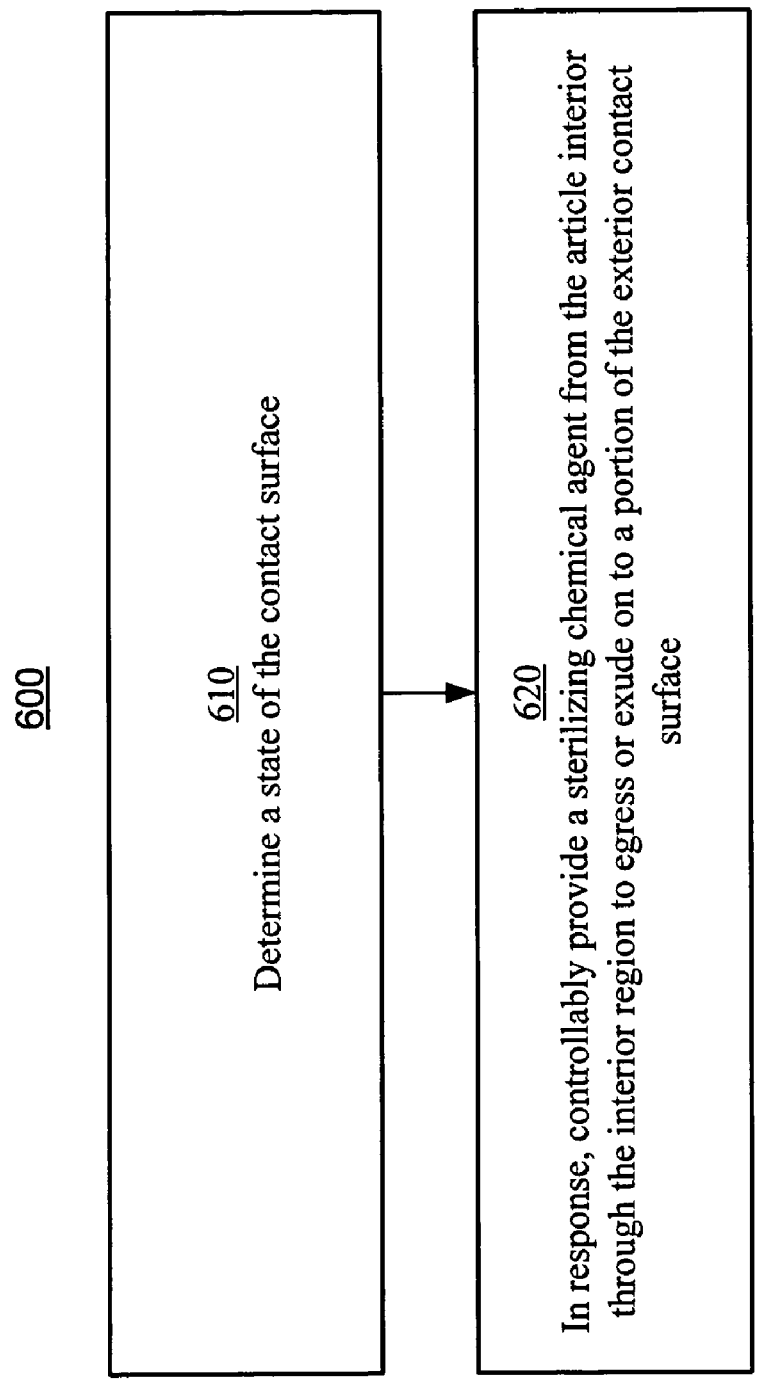

FIGS. 5 and 6 show exemplary features of methods for inhibiting germ transmission from contact surfaces. The methods involve self-sterilization of the contact surfaces.

FIG. 5 shows a method 500 for sterilizing an exterior contact surface disposed on an article, which includes a subsurface or interior region adjacent or contiguous to the exterior contact surface. Method 500 includes: in response to an event, controllably transconducting a sterilizing chemical agent from within the article to a portion of the exterior contact surface through an interior region contiguous to the exterior contact surface (520). The controllable flow is initiated, sustained or terminated, in response to receiving at least one of a contact sensor, a proximity sensor, or a timing sensor signal (510). Method 500 also optionally includes displaying or indicating a status of the contact surface (530).

FIG. 6 shows another method 600 for sterilizing an exterior contact surface disposed on an article body. Method 600 includes determining a state of the contact surface (610), and in response, controllably providing a sterilizing chemical agent from within the article body across an interface between the article body and the contact surface (620). At least a portion of the contact surface is sterilized by action of the sterilizing chemical agent provided from within the article body.

In method 600, determining a state of the contact surface (610) many include determining if a contact has been made to the contact surface, or is likely to be made. Any suitable contact or proximity sensor may be used for this purpose. Additionally or alternatively, determining a state of the contact surface (610) may involve determining if biological materials are present on the contact surface by deploying a bio- or chemical sensor.

Further, in method 600, controllably providing a sterilizing chemical agent from within the article body across an interface between the article body and the contact surface (620) may include flowing the sterilizing chemical agent across the interface through pores or channels in the interface and out through ports or openings in the contact surface. The provision of the sterilizing chemical agent may occur according to a programmed routine or a predetermined schedule Controllably providing a sterilizing chemical agent from within the article body across the interface may include timing of the provision of the sterilizing chemical across the interface, providing the sterilizing chemical agent a predetermined time interval before, during or after a contact is made, providing the sterilizing chemical agent after a predetermined number of contacts, and/or providing the sterilizing chemical agent continuously for a predetermined time interval.

The flow of the sterilizing chemical agent across the interface, in method 600, may be driven by pressure, temperature, surface tension, gravity, a contact-induced pressure or temperature, and/or a pumping device. Contact-actuated power may be utilized to controllably move the sterilizing chemical across the interface. The contact-actuated power may be generated by a movable mechanism, for example, a pressure-activated mechanism. Method 600 may further include storing contact-actuated power to controllably move the sterilizing chemical across the interface at a later time.

Further, method 600 may include supplying the sterilizing chemical agent from an internal chemical supply reservoir, generating the sterilizing chemical agent internally in the article, recovering residual chemicals from the contact surface, and/or storing recovered residual chemicals in a used-chemical reservoir. The controllably provided sterilizing chemical agent may be a chemical which vaporizes at the contact surface, an amine- or hypochlorite-based chemical, an oxidizer, and/or an alcohol.

Like method 500, method 600 also optionally includes displaying or indicating a status of the contact surface. The display may be audio, visual, tactile or any combination thereof.

While various aspects and embodiments have been disclosed herein, other aspects and embodiments will be apparent to those skilled in the art. For example, controlled amounts of sterilizing chemical 104 may be dispensed onto contact surface 101 from within article 100, not merely in response to a sterilization state or condition of the contact surface, but additionally or alternatively in response to movement or orientation of article 100 or portions thereof. Thus, a door knob may be self-sterilized in response to a door closing motion. similarly, a tooth brush may be self-sterilized after it is picked up. A key may be self-sterilized after it is held in horizontal orientation as in a lock keyhole. Similarly, the tooth brush may be self-sterilized after it is placed vertically in a tooth-brush stand.

It will be understood that the various aspects and embodiments disclosed herein are for purposes of illustration and are not intended to be limiting, with the true scope and spirit being indicated by the following claims.

The invention claimed is:

1. A method of sterilizing an article which has an article body and a contact surface disposed thereon, comprising:
    determining a state of the contact surface;
    in response, controllably providing a sterilizing chemical agent from within the article body across an interface between the article body and the contact surface disposed thereon, whereby at least a portion of the contact surface is sterilized by action of the sterilizing chemical agent; and
    resetting a resettable counter for resetting a count of the number of contacts when the number of contacts exceeds a predetermined number after providing the sterilizing chemical agent.

2. The method of claim 1, wherein determining a state of the contact surface comprises determining if a contact has been made to the contact surface.

3. The method of claim 2, wherein determining if a contact has been made comprises deploying any one of a capacitive, a resistive, a mechanical, a piezoelectric, a thermal, an ultrasound, or an optical contact sensor.

4. The method of claim 1, wherein determining a state of the contact surface comprises determining if a contact is proximate.

5. The method of claim 4, wherein determining if a contact is proximate comprises deploying any one of a capacitive, a resistive, a mechanical, a piezoelectric, a thermal, an ultrasound, or an optical proximity sensor.

6. The method of claim 1, wherein determining a state of the contact surface comprises determining if biological materials are present on the contact surface.

7. The method of claim 6, wherein determining if biological materials are present on the contact surface comprises deploying a biosensor.

8. The method of claim 1, wherein controllably providing the sterilizing chemical agent across the interface comprises providing the sterilizing chemical agent according to a programmed routine.

9. The method of claim 1, wherein controllably providing the sterilizing chemical agent across the interface comprises providing the sterilizing in response to a user command.

10. The method of claim 1, wherein controllably providing the sterilizing chemical agent across the interface comprises providing the sterilizing chemical agent upon or after a predetermined number of contacts.

11. The method of claim 1, wherein controllably providing the sterilizing chemical agent across the interface comprises providing the sterilizing chemical agent according to a predetermined schedule.

12. The method of claim 1, wherein controllably providing the sterilizing chemical agent across the interface comprises timing the provision of the sterilizing chemical across the interface.

13. The method of claim 1, wherein controllably providing the sterilizing chemical agent across the interface comprises providing the sterilizing chemical agent a predetermined time interval after a previous provision.

14. The method of claim 1, wherein controllably providing the sterilizing chemical agent across the interface comprises providing the sterilizing chemical agent a predetermined time interval after a contact is made.

15. The method of claim 1, wherein controllably providing the sterilizing chemical agent across the interface comprises providing the sterilizing chemical agent before a contact is made.

16. The method of claim 1, wherein controllably providing the sterilizing chemical agent across the interface comprises providing the sterilizing chemical agent during a contact.

17. The method of claim 1, wherein controllably providing the sterilizing chemical agent across the interface comprises providing the sterilizing chemical agent continuously for a predetermined time interval.

18. The method of claim 1, wherein controllably providing the sterilizing chemical agent across the interface comprises supplying the sterilizing chemical agent from an internal chemical supply reservoir.

19. The method of claim 1, wherein controllably providing the sterilizing chemical agent across the interface comprises generating the sterilizing chemical agent internally in the article.

20. The method of claim 1, further comprising, recovering residual chemicals from the contact surface.

21. The method of claim 20, further comprising, collecting the recovered residual chemicals in a used-chemical reservoir.

22. The method of claim 1, wherein controllably providing a sterilizing chemical agent comprises providing a chemical which vaporizes at the contact surface.

23. The method of claim 1, wherein controllably providing a sterilizing chemical agent comprises providing an amine- or hypochlorite-based chemical.

24. The method of claim 1, wherein controllably providing a sterilizing chemical agent comprises providing an oxidizer.

25. The method of claim 1, wherein controllably providing a sterilizing chemical agent comprises providing an alcohol.

26. The method of claim 1, wherein controllably providing the sterilizing chemical agent across the interface comprises flowing the sterilizing chemical agent across the interface through pores or channels in the interface.

27. The method of claim 1, wherein controllably providing the sterilizing chemical agent across the interface comprises flowing the sterilizing chemical agent through ports or openings in the contact surface.

28. The method of claim 1, wherein the contact surface comprises an impenetrable portion that is devoid of ports or openings through which the sterilizing chemical arrives on the contact surface.

29. The method of claim 1, wherein controllably providing the sterilizing chemical agent across the interface comprises flowing of the sterilizing chemical across the interface under a pressure gradient.

30. The method of claim 1, wherein controllably providing the sterilizing chemical agent across the interface comprises flowing of the sterilizing chemical across the interface under a temperature gradient.

31. The method of claim 1, wherein controllably providing the sterilizing chemical agent across the interface comprises flowing the sterilizing chemical across the interface by surface tension.

32. The method of claim 1, wherein controllably providing the sterilizing chemical agent across the interface comprises flowing the sterilizing chemical across the interface by gravity.

33. The method of claim 1, wherein controllably providing the sterilizing chemical agent across the interface comprises driving the sterilizing chemical across the interface with a contact-induced pressure.

34. The method of claim 1, wherein controllably providing the sterilizing chemical agent across the interface comprises driving the sterilizing chemical across the interface with a contact-induced temperature.

35. The method of claim 1, wherein controllably providing the sterilizing chemical agent across the interface comprises driving the sterilizing chemical across the interface with a pumping device.

36. The method of claim 1, further comprising, using contact-actuated power to controllably move the sterilizing chemical across the interface.

37. The method of claim 36, wherein the contact-actuated power is generated by a movable mechanism.

38. The method of claim 36, wherein the contact-actuated power is generated by a pressure activated mechanism.

39. The method of claim 36, further comprising, storing contact-actuated power to controllably move the sterilizing chemical across the interface at a later time.

40. The method of claim 1, further comprising, using stored power to controllably move the sterilizing chemical across the interface.

41. The method of claim 1, further comprising, receiving power from an external source to controllably move the sterilizing chemical across the interface.

42. The method of claim 1, further comprising, displaying a sterilization state of the contact surface.

43. The method of claim 42, further comprising, providing a tactile, an RF, an audio and/or a visual display of the sterilization state of the contact surface.

44. The method of claim 1, further comprising, displaying a refill state of the sterilizing chemical.

45. The method of claim 44, further comprising, providing a tactile, an RF, an audio and/or a visual display of the refill state of the sterilizing chemical.

* * * * *